United States Patent
Martinez et al.

(10) Patent No.: US 8,939,997 B2
(45) Date of Patent: *Jan. 27, 2015

(54) MEDICAL DEVICES WITH DETACHABLE PIVOTABLE JAWS

(75) Inventors: Michelle D. Martinez, Winston-Salem, NC (US); Vihar C. Surti, Winston-Salem, NC (US); Tyler Evans McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 230 days.

This patent is subject to a terminal disclaimer.

(21) Appl. No.: 13/270,834

(22) Filed: Oct. 11, 2011

(65) Prior Publication Data

US 2012/0109160 A1  May 3, 2012

Related U.S. Application Data

(63) Continuation-in-part of application No. 12/971,873, filed on Dec. 17, 2010.

(60) Provisional application No. 61/391,878, filed on Oct. 11, 2010.

(51) Int. Cl.
*A61B 17/10* (2006.01)
*A61B 17/08* (2006.01)
(Continued)

(52) U.S. Cl.
CPC .................. *A61B 17/10* (2013.01); *A61B 17/08* (2013.01); *A61B 17/122* (2013.01); *A61B 17/1285* (2013.01); *A61B 2017/00473* (2013.01);
(Continued)

(58) Field of Classification Search
CPC ...... A61B 17/08; A61B 17/10; A61B 17/122; A61B 17/128; A61B 17/1285; A61B 2017/00473; A61B 2017/2902; A61B 2017/2931; A61B 2017/2943; A61B 2017/294; A61B 2017/2944
USPC .............. 606/139, 142–143, 205, 1, 206–207
See application file for complete search history.

(56) References Cited

U.S. PATENT DOCUMENTS

| 720,385 A | 2/1903 | Storle |
| 2,614,445 A | 10/1952 | Riordan |

(Continued)

FOREIGN PATENT DOCUMENTS

| DE | 19534320 | 2/1997 |
| DE | 19750878 A1 | 5/1999 |

(Continued)

OTHER PUBLICATIONS

Olympus Endo Therapy brochure on the QuickClip2 Long.
(Continued)

*Primary Examiner* — Julian W Woo
*Assistant Examiner* — Shaun David
(74) *Attorney, Agent, or Firm* — Brinks Gilson & Lione

(57) ABSTRACT

Medical systems, devices and methods are provided for engaging tissue, e.g. for clipping tissue, closing a perforation or performing hemostasis. Generally, the medical system including a housing, first and second jaws rotatable relative to the housing, a driver, and an elongate drive wire. The elongate drive wire may be disconnected from the driver, first and second jaws, and the housing, which are left in vivo engaged with the tissue.

20 Claims, 14 Drawing Sheets

(51) Int. Cl.
    *A61B 17/122* (2006.01)
    *A61B 17/128* (2006.01)
    *A61B 17/00* (2006.01)
    *A61B 17/12* (2006.01)
    *A61B 17/29* (2006.01)

(52) U.S. Cl.
    CPC .......... *A61B2017/12004* (2013.01); *A61B 2017/2902* (2013.01); *A61B 2017/2931* (2013.01); *A61B 2017/2936* (2013.01); *A61B 2017/2943* (2013.01); *A61B 2017/2944* (2013.01)
    USPC .................. 606/142; 606/1; 606/205

(56) References Cited

U.S. PATENT DOCUMENTS

| | | |
|---|---|---|
| 3,958,576 A | 5/1976 | Komiya |
| 4,467,802 A | 8/1984 | Maslanka |
| 4,512,345 A | 4/1985 | Green |
| 4,569,131 A | 2/1986 | Falk et al. |
| 4,733,664 A | 3/1988 | Kirsch et al. |
| 4,763,668 A | 8/1988 | Macek et al. |
| 4,765,335 A | 8/1988 | Schmidt et al. |
| 4,805,618 A | 2/1989 | Ueda et al. |
| 4,950,273 A | 8/1990 | Briggs |
| 5,029,355 A | 7/1991 | Thai |
| 5,100,418 A | 3/1992 | Yoon et al. |
| 5,141,519 A | 8/1992 | Smith et al. |
| 5,152,778 A | 10/1992 | Bales, Jr. et al. |
| 5,174,276 A | 12/1992 | Crockard |
| 5,192,298 A | 3/1993 | Smith et al. |
| 5,201,743 A | 4/1993 | Haber et al. |
| 5,209,747 A | 5/1993 | Knoepfler |
| 5,275,608 A | 1/1994 | Forman et al. |
| 5,275,613 A | 1/1994 | Haber et al. |
| 5,275,615 A | 1/1994 | Rose |
| 5,282,806 A | 2/1994 | Haber et al. |
| 5,318,589 A | 6/1994 | Lichtman |
| 5,368,606 A | 11/1994 | Marlow et al. |
| 5,471,992 A | 12/1995 | Banik et al. |
| 5,571,137 A | 11/1996 | Marlow et al. |
| 5,618,303 A | 4/1997 | Marlow et al. |
| 5,632,764 A | 5/1997 | Beideman et al. |
| 5,702,407 A | 12/1997 | Kaji |
| 5,766,184 A | 6/1998 | Matsuno et al. |
| 5,766,189 A | 6/1998 | Matsuno |
| 5,792,165 A | 8/1998 | Klieman et al. |
| 5,797,923 A | 8/1998 | Aiyar et al. |
| 5,964,779 A | 10/1999 | Mayenberger et al. |
| 6,059,719 A | 5/2000 | Yamamoto et al. |
| 6,358,197 B1 | 3/2002 | Silverman et al. |
| 6,814,742 B2 | 11/2004 | Kimura et al. |
| 6,923,818 B2 | 8/2005 | Muramatsu et al. |
| 7,011,667 B2 | 3/2006 | Kobayashi et al. |
| 7,041,118 B2 | 5/2006 | Muramatsu et al. |
| 7,081,121 B2 | 7/2006 | Muramatsu et al. |
| 7,223,271 B2 | 5/2007 | Muramatsu et al. |
| 7,223,272 B2 | 5/2007 | Francese et al. |
| 7,326,221 B2 | 2/2008 | Sakamoto |
| 7,452,327 B2 | 11/2008 | Durgin et al. |
| 7,488,334 B2 | 2/2009 | Jugenheimer et al. |
| 7,494,461 B2 | 2/2009 | Wells et al. |
| 7,601,159 B2 | 10/2009 | Ewers et al. |
| 7,722,628 B2 | 5/2010 | Stokes et al. |
| 7,727,247 B2 | 6/2010 | Kimura et al. |
| 7,736,372 B2 | 6/2010 | Reydel et al. |
| 7,736,374 B2 | 6/2010 | Vaughan et al. |
| 7,740,639 B2 | 6/2010 | Hummel et al. |
| 7,744,613 B2 | 6/2010 | Ewers et al. |
| 7,766,810 B2 | 8/2010 | Ohdaira |
| 7,776,057 B2 | 8/2010 | Laufer et al. |
| 7,815,652 B2 | 10/2010 | Messerly et al. |
| 8,083,668 B2 | 12/2011 | Durgin et al. |
| 8,088,061 B2 | 1/2012 | Wells et al. |

| | | | |
|---|---|---|---|
| 2002/0151916 A1 | 10/2002 | Muramatsu et al. | |
| 2002/0173805 A1 | 11/2002 | Matsuno et al. | |
| 2002/0177861 A1 | 11/2002 | Sugiyama et al. | |
| 2003/0069592 A1 | 4/2003 | Adams et al. | |
| 2003/0097146 A1* | 5/2003 | Montalvo et al. | 606/205 |
| 2004/0044363 A1 | 3/2004 | Fowler | |
| 2005/0059985 A1 | 3/2005 | Kimura | |
| 2005/0101991 A1 | 5/2005 | Ahlberg et al. | |
| 2005/0234296 A1 | 10/2005 | Saadat et al. | |
| 2005/0251183 A1 | 11/2005 | Buckman et al. | |
| 2005/0272977 A1 | 12/2005 | Saadat et al. | |
| 2006/0084886 A1 | 4/2006 | Reydel | |
| 2006/0155308 A1 | 7/2006 | Griego | |
| 2006/0258905 A1* | 11/2006 | Kaji et al. | 600/106 |
| 2006/0259045 A1 | 11/2006 | Damarati | |
| 2007/0073185 A1 | 3/2007 | Nakao | |
| 2007/0135678 A1* | 6/2007 | Suzuki | 600/37 |
| 2007/0239162 A1 | 10/2007 | Bhatnagar et al. | |
| 2007/0250113 A1 | 10/2007 | Hegeman et al. | |
| 2007/0287993 A1 | 12/2007 | Hinman et al. | |
| 2008/0004656 A1* | 1/2008 | Livneh | 606/205 |
| 2008/0147113 A1 | 6/2008 | Nobis et al. | |
| 2008/0171907 A1 | 7/2008 | Long et al. | |
| 2008/0228199 A1 | 9/2008 | Cropper et al. | |
| 2008/0228202 A1 | 9/2008 | Cropper et al. | |
| 2008/0234703 A1 | 9/2008 | Cropper et al. | |
| 2008/0234705 A1 | 9/2008 | Cropper et al. | |
| 2008/0255427 A1 | 10/2008 | Satake et al. | |
| 2008/0262539 A1 | 10/2008 | Ewers et al. | |
| 2008/0269557 A1 | 10/2008 | Marescaux et al. | |
| 2008/0269566 A1 | 10/2008 | Measamer | |
| 2008/0275441 A1 | 11/2008 | Aue | |
| 2008/0287963 A1 | 11/2008 | Rogers et al. | |
| 2008/0294178 A1 | 11/2008 | Kortenbach et al. | |
| 2008/0300461 A1 | 12/2008 | Shaw et al. | |
| 2008/0300624 A1 | 12/2008 | Schwemberger et al. | |
| 2009/0005638 A1 | 1/2009 | Zwolinski | |
| 2009/0018602 A1 | 1/2009 | Mitelberg et al. | |
| 2009/0043316 A1* | 2/2009 | Durgin et al. | 606/142 |
| 2009/0062792 A1 | 3/2009 | Vakharia et al. | |
| 2009/0138006 A1 | 5/2009 | Bales et al. | |
| 2009/0138028 A1 | 5/2009 | Wells et al. | |
| 2009/0143794 A1 | 6/2009 | Conlon et al. | |
| 2009/0163934 A1 | 6/2009 | Raschdorf, Jr. et al. | |
| 2009/0192344 A1 | 7/2009 | Bakos et al. | |
| 2009/0221915 A1 | 9/2009 | Voegele et al. | |
| 2009/0299385 A1 | 12/2009 | Stefanchik et al. | |
| 2009/0306683 A1 | 12/2009 | Zwolinski et al. | |
| 2009/0306686 A1 | 12/2009 | Ohdaira | |
| 2009/0326518 A1 | 12/2009 | Rabin | |
| 2009/0326578 A1 | 12/2009 | Ewers et al. | |
| 2010/0042115 A1 | 2/2010 | Saadat et al. | |
| 2010/0057078 A1 | 3/2010 | Arts et al. | |
| 2010/0057085 A1 | 3/2010 | Holcomb et al. | |
| 2010/0130817 A1 | 5/2010 | Conlon | |
| 2010/0168787 A1 | 7/2010 | Surti | |
| 2010/0179540 A1 | 7/2010 | Marczyk et al. | |
| 2010/0198149 A1 | 8/2010 | Fox | |
| 2010/0198248 A1 | 8/2010 | Vakharia | |
| 2010/0211086 A1 | 8/2010 | Ewers et al. | |
| 2010/0217151 A1 | 8/2010 | Gostout et al. | |
| 2010/0217292 A1 | 8/2010 | Kimura et al. | |
| 2010/0217293 A1 | 8/2010 | Kimura et al. | |
| 2010/0217294 A1 | 8/2010 | Kimura et al. | |
| 2010/0249498 A1 | 9/2010 | Wingardner et al. | |
| 2010/0249700 A1 | 9/2010 | Spivey | |
| 2010/0249808 A1 | 9/2010 | Harada et al. | |
| 2012/0016391 A1 | 1/2012 | Aguirre | |
| 2012/0089158 A1 | 4/2012 | Martinez et al. | |
| 2012/0109160 A1 | 5/2012 | Martinez et al. | |
| 2012/0165863 A1 | 6/2012 | McLawhorn | |

FOREIGN PATENT DOCUMENTS

| | | |
|---|---|---|
| DE | 19906360 A1 | 8/2000 |
| DE | 102006003548 | 8/2007 |
| JP | 57-156752 | 9/1982 |
| JP | 60-103946 | 6/1985 |
| JP | 63-6016 | 2/1988 |

(56) References Cited

FOREIGN PATENT DOCUMENTS

| | | |
|---|---|---|
| JP | 63-267345 | 11/1988 |
| JP | 63-288147 | 11/1988 |
| JP | 2-6011 | 1/1990 |
| JP | 2007950 | 1/1990 |
| JP | 4-26091 | 3/1992 |
| JP | 4102450 | 4/1992 |
| JP | 5-212043 | 8/1993 |
| JP | 5208020 | 8/1993 |
| JP | 5212042 | 8/1993 |
| JP | 6237939 | 8/1994 |
| JP | 6254101 | 9/1994 |
| JP | 8019548 | 1/1996 |
| JP | 8126648 | 5/1996 |
| JP | 8280701 | 10/1996 |
| JP | 8308847 | 11/1996 |
| JP | 9038093 | 2/1997 |
| JP | 9289989 | 11/1997 |
| JP | 2000-33090 | 2/2000 |
| JP | 2000-335631 | 12/2000 |
| JP | 2001-520069 | 10/2001 |
| JP | 2002-224124 | 8/2002 |
| JP | 2002-301082 | 10/2002 |
| JP | 2002-360585 | 12/2002 |
| WO | WO 9614020 | 5/1996 |
| WO | WO 99/20183 | 4/1999 |
| WO | WO 2004/017839 | 4/2004 |
| WO | WO 2008/005433 | 1/2008 |
| WO | WO 2010/078163 | 7/2010 |
| WO | WO 2011/087723 | 7/2011 |
| WO | WO 2012/051188 | 4/2012 |
| WO | WO 2012/051200 | 4/2012 |
| WO | WO 2012/083041 | 6/2012 |
| WO | WO2012/051200 | 11/2012 |

OTHER PUBLICATIONS

Cooper Surgical brochure on the Marlow Nu-Tip Laparoscopic Instruments.
Medwork brochure,Endo Therapy for the Clipmaster 3.
Boston Scientific Catalog on the Resolution Clip Device.
Medicon Instrument Catalog, pp. 440, 441, 443, 451, 585, 686 (1986).
V. Mueller, The Surgical Armamentarium, pp. F176-F177 (1988).
Annex to Form PCT/ISA/206—Communication Relating to the Results of Partial International Search for PCT/US2011/055800 (Jun. 28, 2012).
International Search Report/Written Opinion for PCT/US2009/069270 (May 17, 2010).
International Search Report/Written Opinion for PCT/US2010/061077 (Apr 1, 2011).
International Search Report and Opinion for PCT/US2011/055780 (Jun. 14, 2012).
International Search Report and Opinion for PCT/US2011/055786 (Jun. 19, 2012).
International Search Report and Opinion for PCT/US2011/065200 (Jun. 13, 2012).
International Search Report and Opinion for PCT/US2011/055800 (Sep. 12, 2012).
International Search Report and Opinion for PCT/US2012/046666 (Oct. 8, 2012).
Office Action dated Jan. 18, 2012 for U.S. Appl. No. 12/645,004 in related application.
Office Action dated May 29, 2012 for U.S. Appl. No. 12/645,004 in related application.
Office Action dated Dec. 20, 2012 for U.S. Appl. No. 13/186,427 in related application.

\* cited by examiner

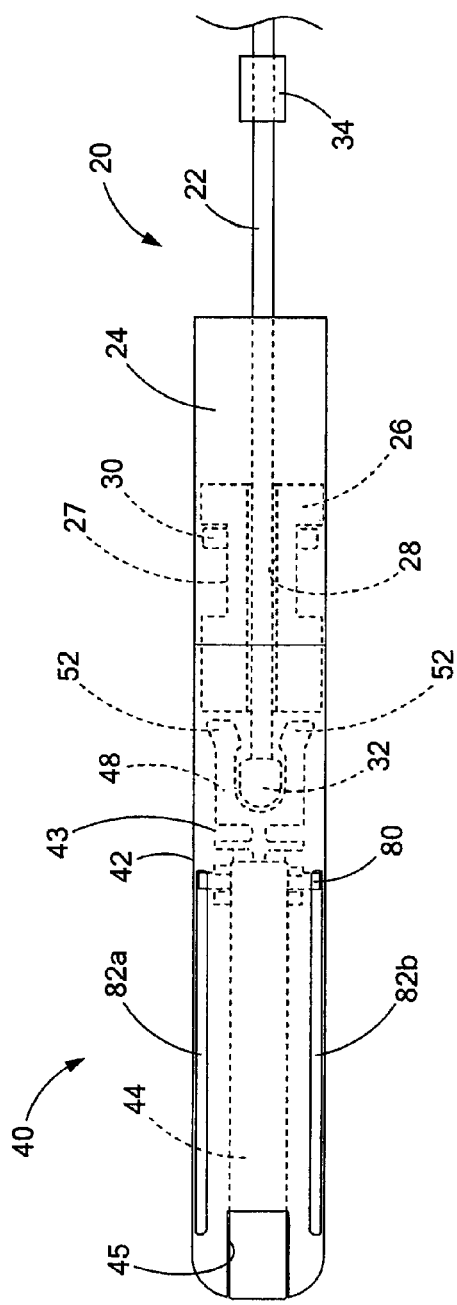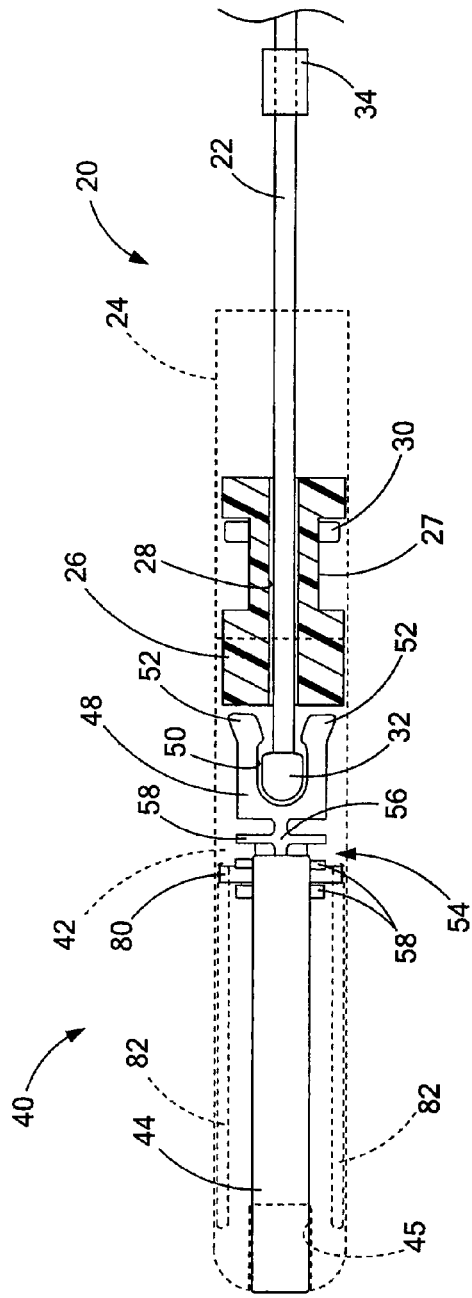
FIG. 1
FIG. 2

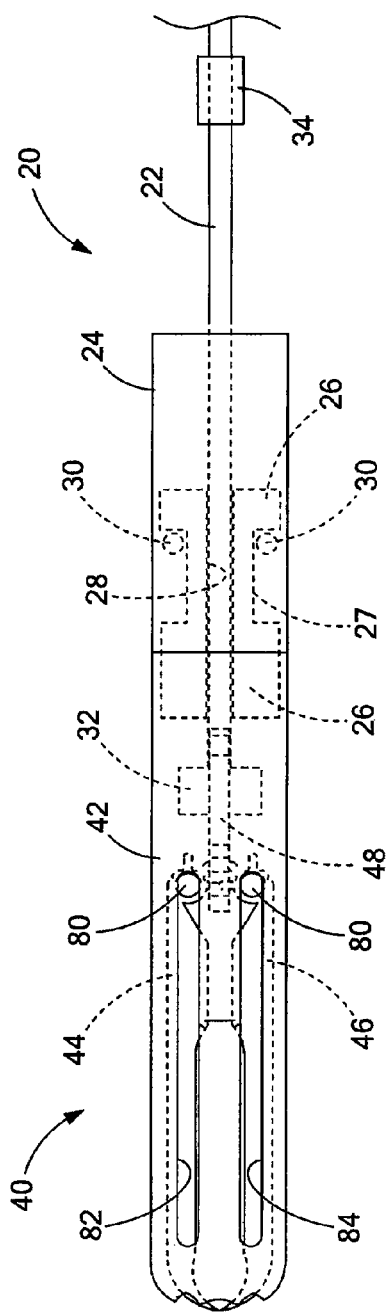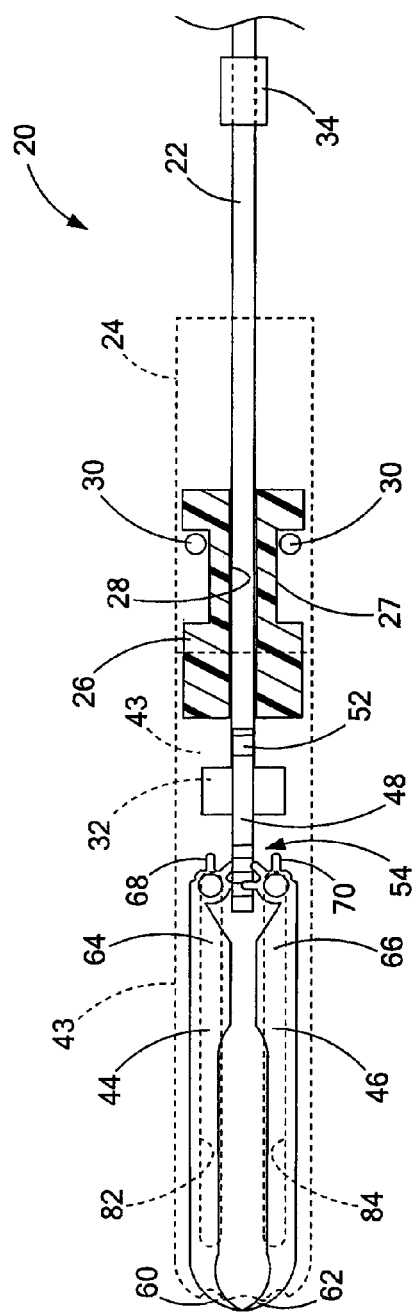

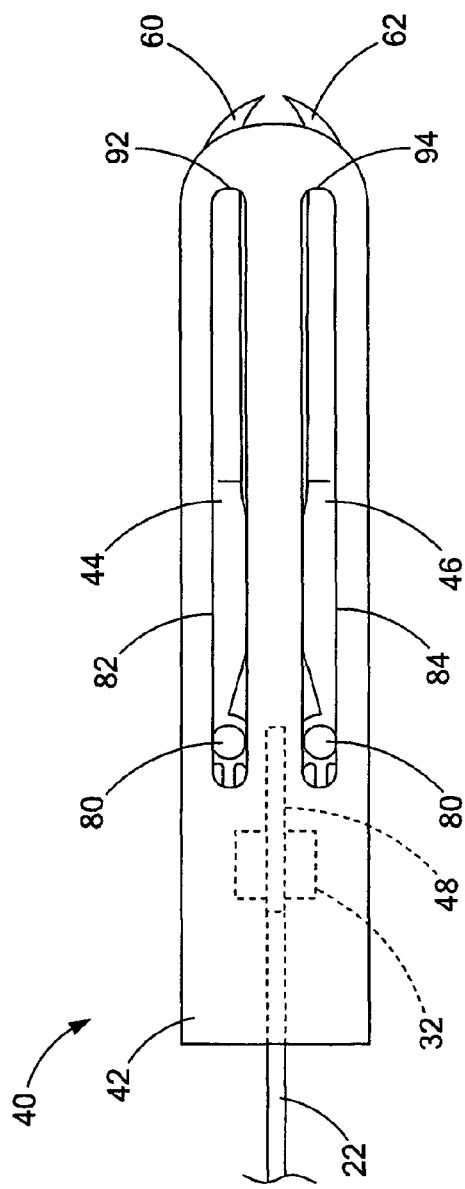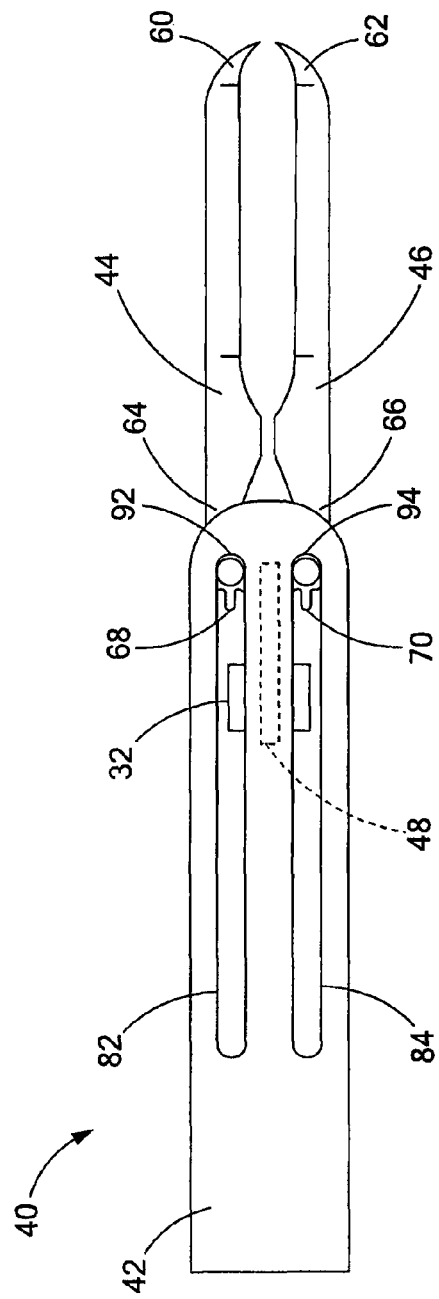
FIG. 8
FIG. 9

MEDICAL DEVICES WITH DETACHABLE PIVOTABLE JAWS

CROSS-REFERENCE TO RELATED APPLICATIONS

This application is a Continuation-In-Part of U.S. patent application Ser. No. 12/971,873 filed on Dec. 17, 2010, and also claims the benefit of U.S. Provisional Patent Application Ser. No. 61/391,878 filed on Oct. 11, 2010. All of the foregoing applications are hereby incorporated by reference.

BACKGROUND

Conventionally, a clip may be introduced into a body cavity through an endoscope to grasp living tissue of a body cavity for hemostasis, marking, and/or ligating. Such clips are often known as surgical clips, endoscopic clips, hemostasis clips and vascular clips. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding. Clips have also been attempted for use in closing perforations in the stomach Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices such as clips have been used in various parts of the body, including gastrointestinal applications. One of the problems associated with conventional hemostatic devices and clips, however, is that many devices are not strong enough to cause permanent hemostasis. Further, clips have also been attempted for use in closing perforations in the stomach or gastrointestinal structures, but unfortunately traditional clips suffer from difficult placement and the capability to grasp a limited amount of tissue, potentially resulting in incomplete closure.

SUMMARY

The invention may include any of the following aspects in various combinations and may also include any other aspect described below in the written description or in the attached drawings.

In a first aspect, a medical device is provided for engaging tissue, the medical device including a housing, first and second jaws, a driver, an elongated drive wire and an elongated tubular member. The housing defines an internal passageway and a longitudinal axis extending between proximal and distal ends of the housing. The first and second jaws are rotatable relative to the housing and have proximal and distal ends. The driver is engaged with the proximal ends of the first and second jaws, wherein longitudinal movement of the driver rotates the first and second jaws relative to the housing. The elongated drive wire is selectively connected to the driver for longitudinal movement therewith, and the drive wire has an enlarged portion proximate a distal end of the drive wire. The elongate tubular member defines a lumen sized to slidably receive a connection block. The connection block defines a bore slidably receiving the drive wire, wherein the enlarged portion of the drive wire has a size that is larger than the bore and is positioned on a distal side of the connection block. The connection block is operable between an extended position and a retracted position. The connection block projects from the tubular member in the extended position and is structured to engage a proximal end of the housing. The connection block is positioned within the lumen of the tubular member in the retracted position and disengaged from the housing. The enlarged portion of the drive wire engages the connection block upon proximal retraction of the drive wire to operate the tubular member from its extended position to its retracted position and disengage the connection block from the housing.

According to further detailed aspects, the connection block is preferably sized to frictionally engage the housing. The connection block may include a connection ring having a plurality of tabs, wherein the housing includes a plurality of slots extending to a proximal end of the housing that receive the plurality of tabs. The plurality of slots may each include a narrowed throat separating proximal and distal portions of the slots. The housing may further include a plurality of slits formed therein, the slits each connected to a distal portion of the slots to improve flexibility of the housing. The connection block includes a distal flange and a proximal flange defining a reduced diameter portion therebetween, and the tubular member includes one of a pin and a tab projecting into the lumen and positioned within the reduced diameter portion to limit longitudinal movement of the connection block. The connection block may also include a compressible member attached thereto and sized to be compressed between an interior of the housing and an exterior of the connection block.

According to further detailed aspects, the system may also include an attachment member attached to a distal end of the tubular member, the attachment member including a passageway in communication with the lumen of the tubular member. The attachment member preferably includes diametrically opposing openings between ends of the attachment member in communication with the passageway. The connection block includes a distal flange and a proximal flange defining a reduced diameter portion therebetween, and the attachment member preferably includes at least one tab projecting into the lumen and positioned within the reduced diameter portion to limit longitudinal movement of the connection block, the tab unitarily and integrally formed with the attachment member. The system may also include a locking pin having a forked strut defined by two tines having a slot therebetween. The slot is sized to receive the drive wire therein, and the forked strut sized to pass through the opposing openings in the attachment member and limit longitudinal movement of the connection block. The system may still further include an applicator having a left body slidably attached to a right body, the left and right bodies including channels sized and shaped to receive portions of the tubular member and attachment member and maintain their position relative to the applicator. The channels are also sized and shaped to receive portions of the locking pin, whereby relative translation of the left and right bodies positions the forked strut of the locking pin into, or out of, the opposing openings in the attachment member. Alternatively, the applicator may simply have a main body and a forked strut projecting from the main body, the forked strut defined by two tines having a slot therebetween, the slot sized to receive the drive wire therein, the forked strut sized to pass through the opposing opening in the attachment member and limit longitudinal movement of the connection block.

According to still further detailed aspects, the enlarged portion of the drive wire is an enlarged distal head, and the driver includes a socket facing proximally and receiving the distal head. The driver is constructed of a resilient material that flexes to adjust the size of the socket. The socket is sized to selectively receive the enlarged distal head of the drive wire. A locking tab may be positioned at an entrance to the socket and moves to vary the size of the entrance. Preferably, the driver includes two locking tabs on opposing sides of the socket, and the housing includes a guide surface guiding the longitudinal movement of the driver, the guide surface including two surfaces on opposing sides of the housing corresponding to the two locking tabs. The housing may also define a shoulder at the transition between the proximal portion and distal portion of the guide surface, wherein the locking tab is positioned to engage the shoulder to limit longitudinal movement of the driver. The shoulder preferably deflects the tab to a position into engagement with the shoulder when a distally directed longitudinal force on the driver reaches a predetermined force to permit longitudinal movement of the driver and the first and second jaws in a distal direction.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a top view of a medical system having a medical device for engaging tissue, constructed in accordance with the teachings of the present invention;

FIG. 2 is a top view similar to FIG. 1, but showing the outer structures in dotted lines and the interior sections in solid lines and partial cross section;

FIG. 3 is a side view of the medical system and device depicted in FIG. 1;

FIG. 4 is a side view similar to FIG. 3, but showing the outer structures in dotted lines and the interior structures in solid lines and partial cross section

FIGS. 8-12 are side views showing operation of the medical system and device depicted in FIGS. 1-5;

DETAILED DESCRIPTION

Figure 5:
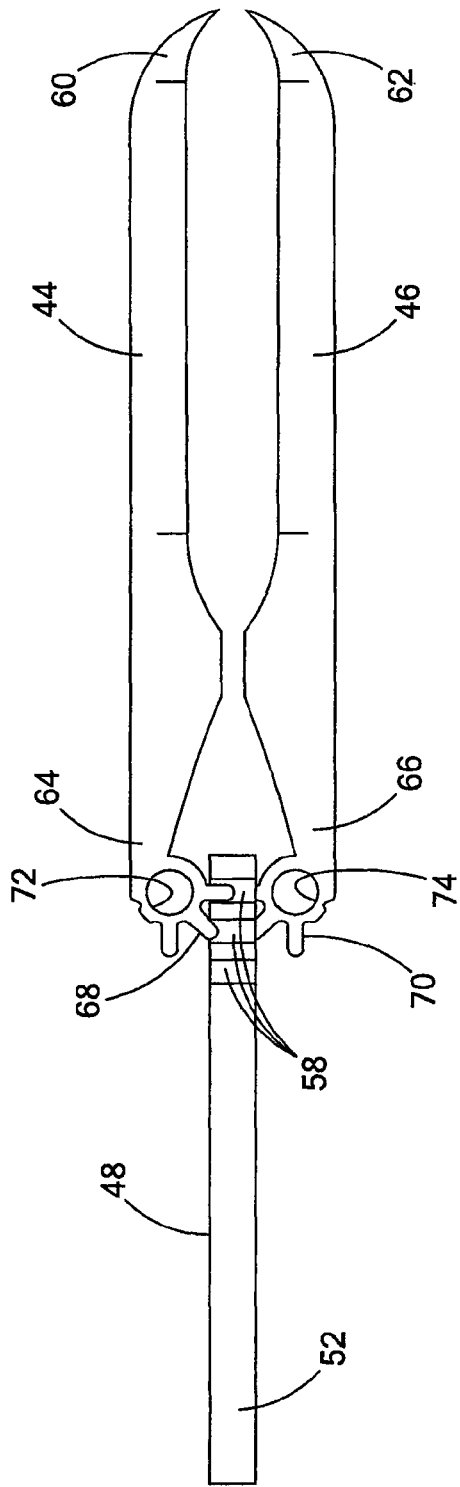
FIG. 5 is a side view of a medical device that is part of the medical system depicted in FIGS. 1-4.

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

An exemplary medical system 20 having a medical device 40 for engaging tissue T (FIG. 11) is shown in FIGS. 1 through 4. The medical system 20 and device 40 are generally sized and structured for operation through the working channel of an endoscope (not shown) or other scope, although the system 20 and device 40 may also be used alone or in conjunction with other elongate devices such as catheters, fiber-optic visualization systems, needles and the like. Generally, the medical system 20 includes a drive wire 22 slidably housed within the distal end 23 of an elongated catheter 24 for selective connection to, and operation of, the medical device 40. As will be described in further detail herein, the medical device 40 generally includes a housing 42 having a first jaw 44 and a second jaw 46 pivotally connected thereto for engaging the tissue T. Generally, the jaws 44, 46 have been shown as forming grasping forceps, although the jaws are intended to be used to clip tissue, e.g. to close an opening or for hemostasis. Accordingly, it will be recognized that the shape and structure of the jaws may take many forms and serve many purposes and functions, all in accordance with the teachings of the present invention.

In the medical system 20, the drive wire 22 slidably extends through the catheter 24. Although the term "wire" is used to refer to the drive wire 22, it will be recognized that any elongate control member capable of transmitting longitudinal force over a distance (such as is required in typical endoscopic, laparoscopic and similar procedures) may be used, and this includes plastic rods or tubes, single filament or multi-filament wires and the like. A connection block 26 is slidably fitted within the distal end 23 of the catheter 24 and defines a bore 28 therethrough which slidably receives the drive wire 22. The exterior of the connection block 26 includes a recessed portion 27, and two pins 30 (e.g., formed from stainless steel wire) are connected to the catheter 24 and positioned within the recessed portion 27 to limit the longitudinal movement of the connection block 26.

A distal end of the drive wire 22 defines a distal head 32 that is sized larger than the drive wire 22, and likewise larger than the bore 28 in the connection block 26. As will be described later herein, the distal head 32 is used to slide the connection block 26 within the catheter 24 to disconnect the medical device 40 from the medical system 20. As also seen in FIGS. 1-4, the housing 42 of the medical device 40 is a tubular member defining an interior space 43. A proximal end of the housing 42 frictionally receives a distal end of the connection block 26 within the interior space 43 for selective connection therewith.

The internal passageway 43 of the housing 42 also receives the first and second jaws 44, 46 and a driver 48 which is used to interconnect the drive wire 22 to the jaws 44, 46. As best seen in FIGS. 1, 2 and 5, the driver 48 has a proximal portion which defines a socket 50 sized to receive enlarged distal head 32 of the drive wire 22. At the proximal entrance of the socket 50, two deflectable locking tabs 52 are formed which rotate relative to the remainder of the driver 48 to increase or decrease the size of the socket 50. The locking tabs 52 may be separately formed and pivotally attached to the driver 48, or may be integrally formed with the driver 48 and formed of a resilient material which flexes to permit rotation of the locking tabs 52 radially inwardly and radially outwardly. Preferably the locking tabs 52 are plastically deformable, such that they may be locked to the drive wire 22 or to the housing 42, as discussed further herein.

A distal portion of the driver 48 defines a rack 54 for engaging and operating the jaws 44, 46. In the depicted embodiment, the rack 54 includes a central spine 56 having teeth 58 projecting away from the central spine 56 and on opposite sides of the spine 56. One set of teeth 58 on one side of the spine 56 generally operate the first jaw 44 while the other set of teeth 58 on the other side of the spine 56 operate the second jaw 46. It will be recognized that the rack 54 may include a single set of teeth or other geared structures that interface with the jaws 44, 46.

As best seen in FIG. 5, the first and second jaws 44, 46 include distal ends 60, 62 that are structured to grasp and engage tissue, generally they have a talon shape as disclosed in 61/141,934 filed Dec. 31, 2008, the disclosure of which is incorporated herein by reference in its entirety. The proximal ends 64, 66 of the first and second jaws 44, 46 each include a pinion gear 68, 70 having a series of teeth. The teeth of the pinion 68, 70 mesh with the teeth of the rack 54 of the driver 48 such that longitudinal translation of the driver 48 induces rotation in the first and second jaws 44, 46 relative to one another. Generally, distal translation of the driver 48 causes the first and second jaws 44, 46 to rotate outwardly away from each other, while proximal retraction of the driver 48 causes the first and second jaws 44, 46 to rotate inwardly toward one another. Pins 80 are fitted through each the proximal ends of the jaws 44, 46, to pivotally connect the jaws to the housing 42. Other structures for forming a pivotal connection may be used, and preferably the pivotal connection is centrally arranged relative to the pinions 68, 70.

Figure 7:
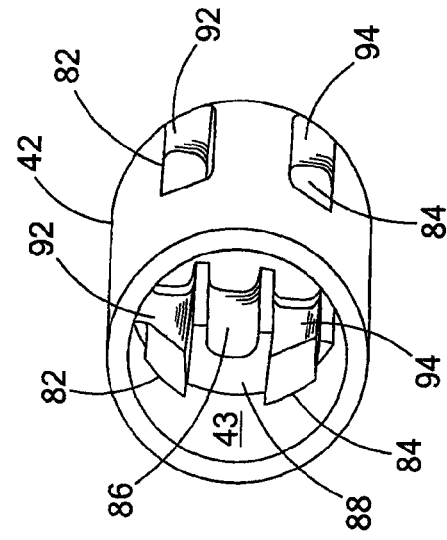
FIG. 7 is a perspective view of the housing depicted in FIG. 6.
Figure 6:
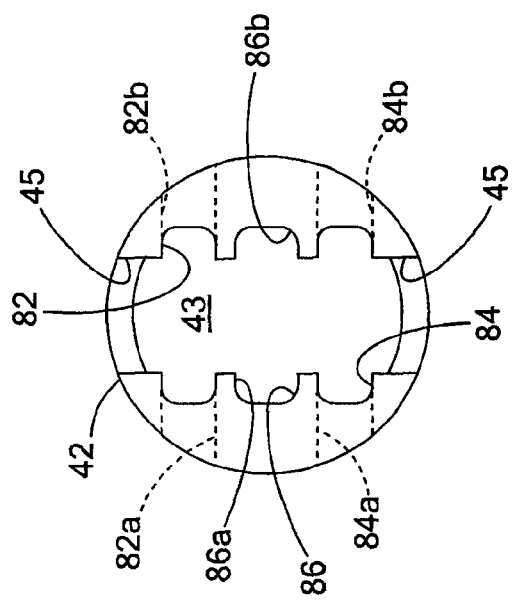
FIG. 6 is a front view of a housing forming a portion of the medical system and device depicted in FIGS. 1-5.

In addition to the jaws 44, 46 being pivotally attached to the housing 42, the first and second jaws 44, 46 are also slidably attached to the housing 42. As best seen in FIGS. 6 and 7 (and in conjunction with FIGS. 1-4) the housing 42 defines a first guide surface 82 for the first jaw 44, and a second guide surface 84 for the second jaw 46. As seen in FIG. 3, the first and second guide surfaces 82, 84 are formed by elongated slots 82a, 82b, 84a, 84b formed in opposing sides of the housing 42 which leaves a thickness of the housing 42 exposed to serve as the guide surface. The slots 82a, 82b are aligned to receive the connecting pin 80 of the first jaw 44, and likewise the slots 84a, 84b are aligned to receive the connecting pin 80 of the second jaw 46. The ends of the slots, for example distal ends 92, 94 shown in FIG. 7, serve to restrict the longitudinal movement of the jaws 44, 46 relative to the housing 42. The proximal ends 64, 66 of the jaws 44, 46 include apertures 72, 74 which receive the pins 80 (FIGS. 1, 2 and 3) that are used to slidably and pivotally connect the first and second jaws 44, 46 to the housing 42.

It can also be seen in FIGS. 6 and 7 that the housing 42 defines a third guide surface 86 which guides the longitudinal movement of the driver 48 within the housing 42. The guide surface 86 in the depicted embodiment includes a left guide surface 86a and a right guide surface 86b formed as C-shaped channels. As shown in FIG. 7, the third guide surface 86 transitions from a smaller proximal width to a larger distal width to define a shoulder 88 at the transition, which will be further described hereinbelow with reference to FIGS. 13 and 14.

As also shown in FIG. 6, the internal passageway 43 of the housing 42 extends through the distal end of the housing, and through which the first and second jaws 44, 46 can extend. Additionally, as shown in FIGS. 1 and 2, the housing 42 defines opposing slots 45 which are sized to permit the first and second jaws 44, 46 to pass therethrough when they rotate radially outwardly. Accordingly, it is also clear from FIGS. 1 and 2 that the housing 42 serves to block rotation of the first and second jaws 44, 46 when they are entirely or partially contained within the internal passageway 43 of the housing 42. Suitable plastics for forming the housing include, but are not limited to, polytetrafluoroethylene (PTFE), expanded polytetrafluoroethylene (EPTFE), polyethylene ether keytone (PEEK), polyvinylchloride (PVC), polycarbonate (PC), polyamide, polyimide, polyurethane, polyethylene (high, medium or low density), and suitable metals include stainless steel, nitinol and similar medical grade metals and alloys.

Operation of the medical device 40 will now be described with reference to FIGS. 8-12. As shown in FIG. 8, the first and second jaws 44, 46 are shown in a retracted position where they are substantially contained within the housing 42. Depending on the application, the distal ends 60, 62 of the jaws 44, 46 may slightly project from the distal end of the jaws 44, 46 in their retracted positions, or they may be entirely positioned within the housing 42. When the drive wire 22 is translated distally (to the right on the page in FIG. 8) the distal head 32 engages the driver 48, and since the rack 54 of the driver 48 is meshed with the pinions 68, 70 at the proximal ends 64, 66 of the jaws 44, 46, the driver 48 and jaws 44, 46 slide distally through the housing 42 because the housing 42 blocks their rotation. As previously mentioned, this longitudinal movement is guided by the first and second guide surfaces 82, 84 which receive the pins 80 that slidably and pivotally connect the jaws 44, 46 to the housing 42.

Figure 10:
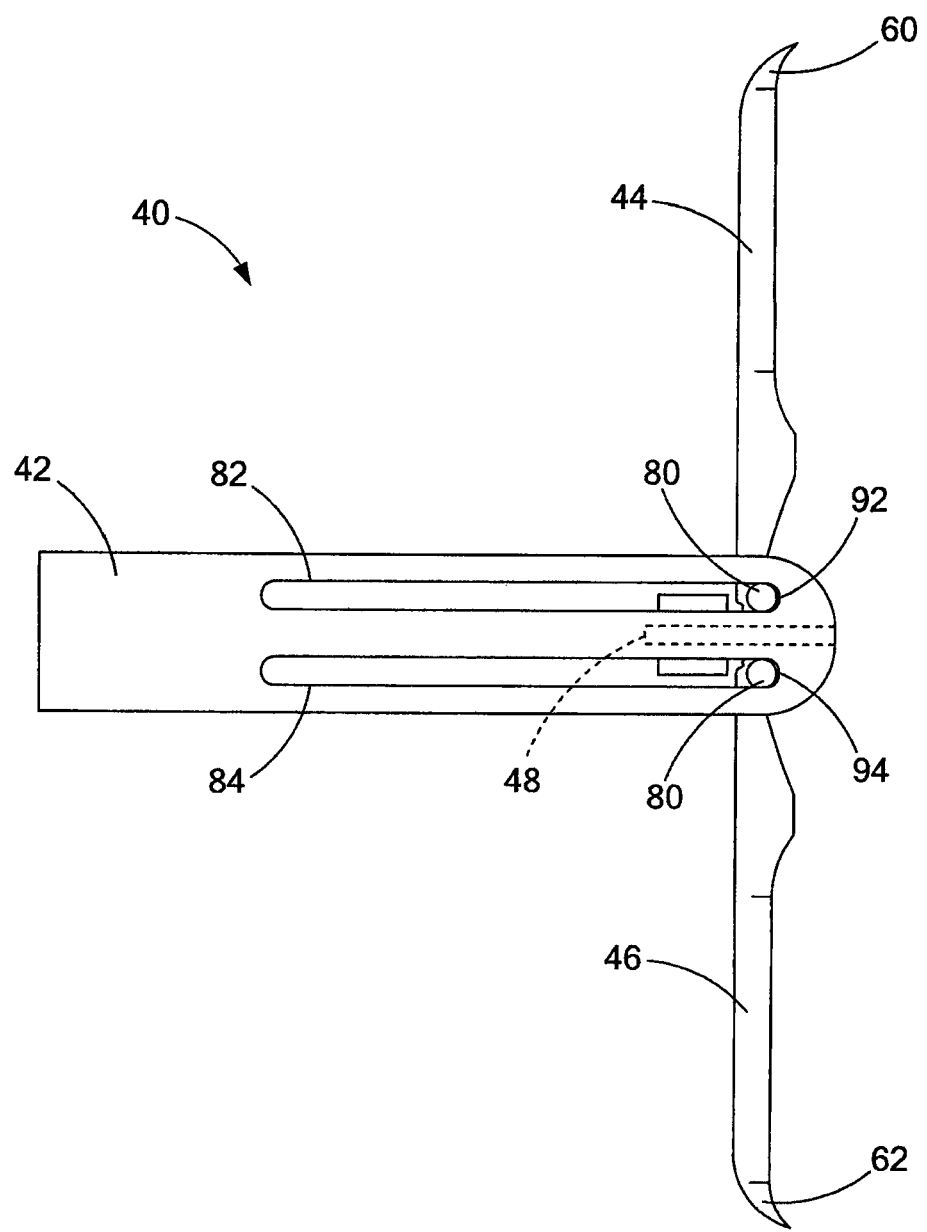

As shown in FIG. 9, the first and second jaws 44, 46 have an extended position where the jaws substantially project from a distal end of the housing 42, and their proximal ends 64, 66 are positioned adjacent the distal end of the housing 42. Accordingly, it will be seen that further distal advancement of drive wire 22, and hence the driver 48, causes the pinion 68 to rotate over the teeth 58 of the rack 54. As best seen in FIG. 10, the first and second jaws 44, 46 rotate radially outwardly from each other into a tissue receiving position. Notably, due to the presence of slots 45 at the distal end of the housing 42, the jaws 44, 46 are permitted to rotate a full 90°, thus forming at least a 180° between them. It will be recognized that through the sizing of the slots 45 and the construction of the rack 54 and pinions 68, 70, the first and second jaws 44, 46 may rotate even further away from each other.

Figure 11:
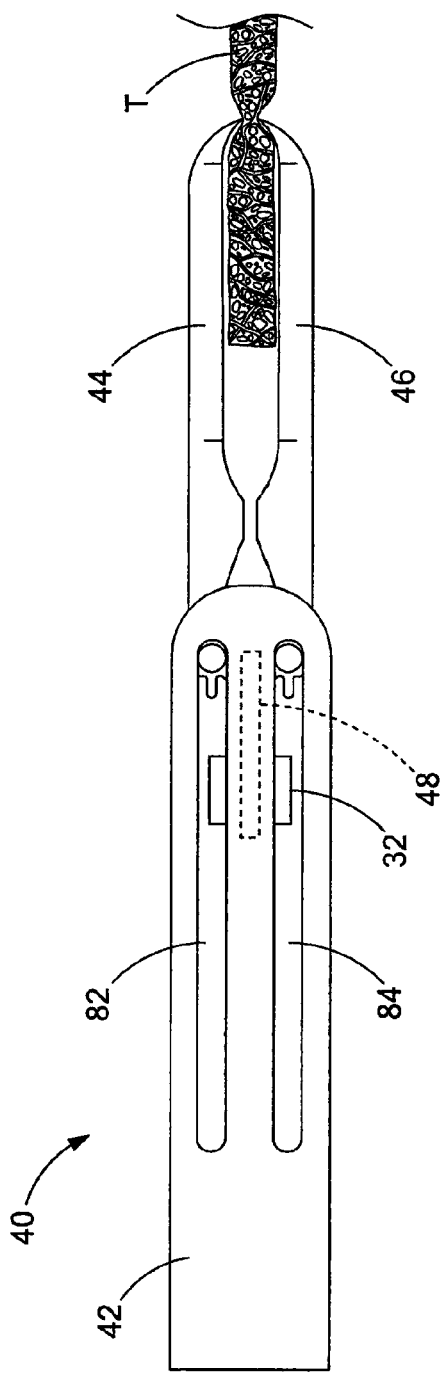
Figure 12:
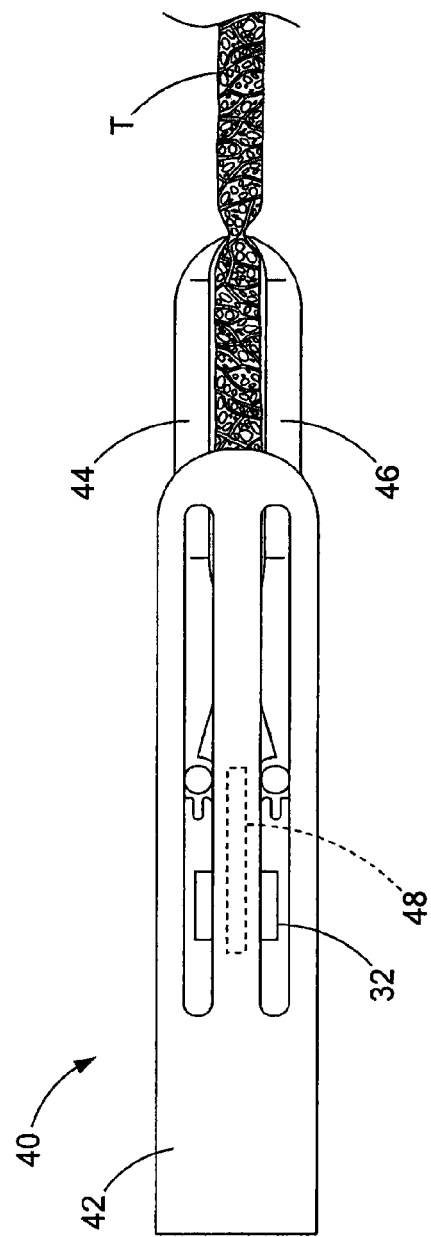

In the tissue receiving configuration shown in FIG. 10, the medical device 40 and its jaws 44, 46 may be positioned adjacent tissue T. As shown in FIG. 11, the tissue T may be placed between the first and second jaws 44, 46 and the jaws 44, 46 rotated back towards their position shown in FIG. 9. The tissue T has been shown as a single layer, although multiple layers may be clipped between the jaws 44, 46. Generally, proximal retraction of the drive wire 22 and the driver 48 again causes rotation of the first and second jaws 44, 46 to grasp the tissue T therebetween. As shown in FIG. 12, further proximal retraction of the drive wire 22 and driver 48 will cause the jaws 44, 46 to move longitudinally in a proximal direction (to the left on the page in FIG. 12).

Figure 13:
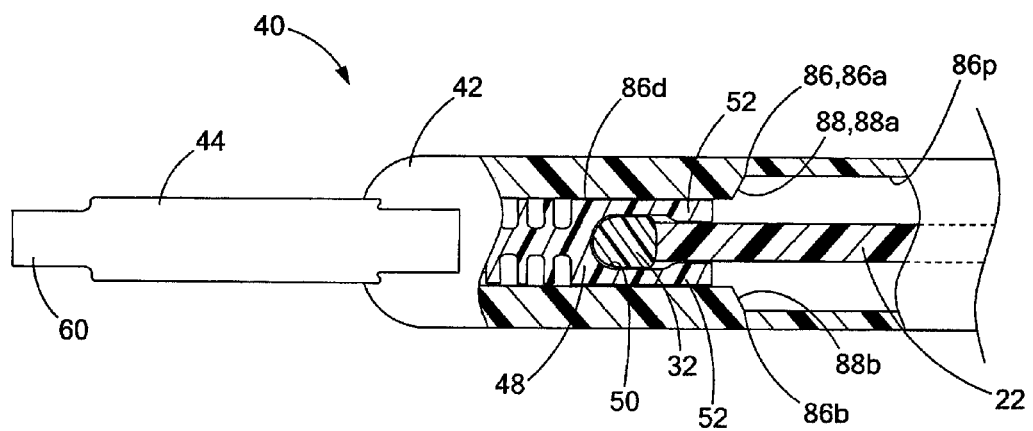
FIGS. 13 and 14 are top views, partially in cross-section, depicting operation of the medical system and device depicted in FIGS. 1-4.
Figure 14:
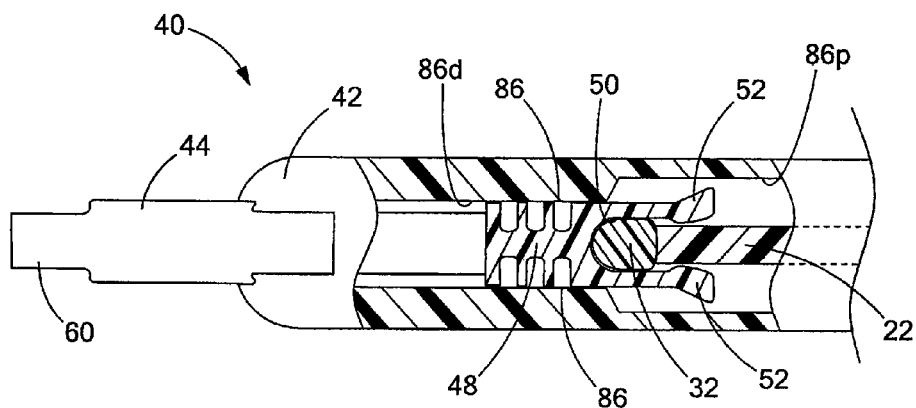

In order for the medical device 40 to serve as a clip and maintain its grasp on the tissue T, or to maintain the clipping of two layers of tissue against each other, the jaws 44, 46 may be locked in position and the drive wire 22 of the medical system 20 disconnected from the medical device 40. As shown in FIG. 13, the third guide surface 86 (which guides the driver 48) includes a proximal portion 86p and a distal portion 86d. The proximal portion 86p of the third guide surface 86 has a width (measured up and down on the page in FIG. 13) that is greater than a width of the distal portion 86d of the third guide 86. As previously discussed, the third guide surface 86 is formed by opposing surfaces or C-shaped channels 86a, 86b of the housing 42. The transition between the proximal portion 86p and distal portion 86d defines a shoulder 88, and namely two shoulders 88a, 88b on opposing sides of the housing 42. The shoulders 88a, 88b are sized and positioned to engage the locking tabs 52 located on the driver 48.

As shown in FIG. 13, when the driver 48 is located within the distal portion 86d of the third guide surface 86, the locking tabs 52 are forced radially inwardly into firm frictional engagement with the drive wire 22. Stated another way, the socket 50 formed by the driver 48 to receive the distal head 32 has an entrance which is narrowed by the inward deflection of the locking tabs 52. In this state depicted in FIG. 13, the drive wire 22 is firmly engaged with the driver 48 and hence the first and second jaws 44, 46. When the drive wire 22 and driver 48 are retracted proximally, for example upon grasping tissue as shown in FIG. 12, the proximal end of the driver 48 is received within the proximal portion 86p of the third guide surface 86 which has a larger width that permits outward movement of the locking tabs 52. Accordingly, in the state depicted in FIG. 14, the locking tabs 52 may be loosely and detachably connected to the distal head 32 of the drive wire 22. That is, the proximal retraction of the jaws 44, 46 will be limited by either the tissue T engaging the distal end of the housing 42, or the pins 80 will abut the proximal ends of the slots 82a, 82b, 84a, 84b defining a first and second guide surfaces 82, 84. As such, when proximal movement of the jaws 44, 46 and the driver 48 are thus limited, further proximal movement of the drive wire 22 and its distal head 32 may be used to withdraw the distal head 32 from the socket 50 of the driver 48. This operation may also be used to further deflect the locking tabs 52 radially outwardly, e.g. via plastic deformation into this outward position to maintain the closed configuration of the jaws. In the event the natural elasticity of the tissue T tends to pull the jaws 44, 46 out from the housing towards their extended position, the locking tabs 52 will abut the shoulders 88a, 88b of the third guide surface of the housing 42 to prevent further distal movement of the jaws 44, 46.

Figure 15:
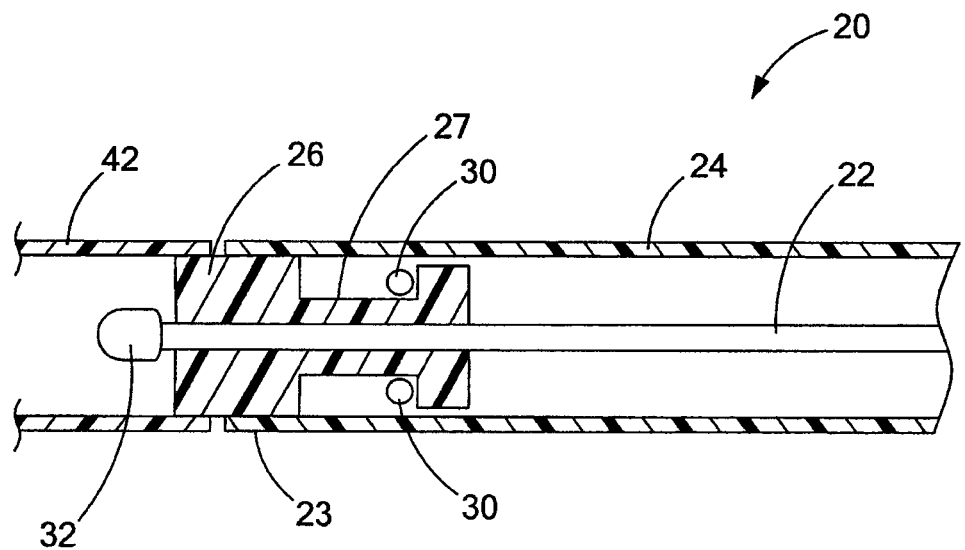
FIGS. 15 and 16 are cross-sectional views showing operation of the medical system depicted in FIGS. 1-4.
Figure 16:
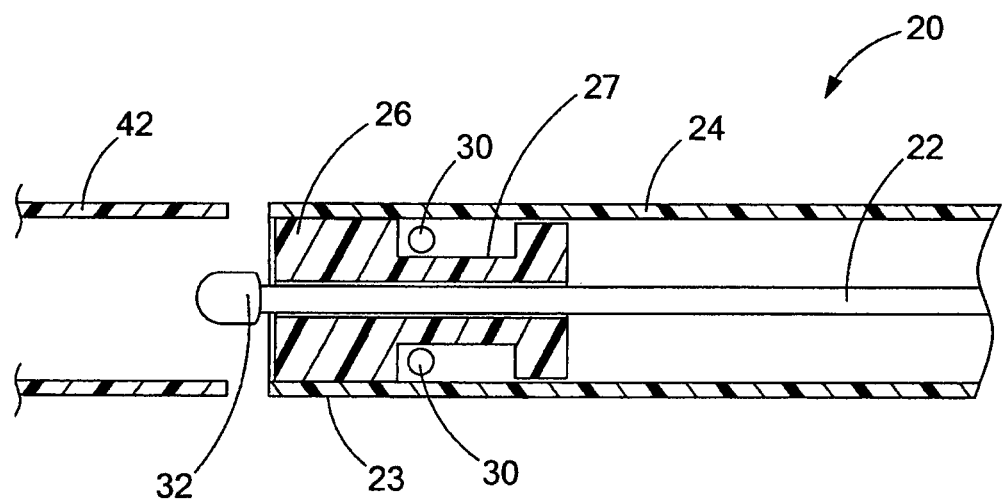

Turning now to FIGS. 15 and 16, upon still further proximal retraction of the drive wire 22 and distal head 32, the enlarged distal head 32 will abut the connection block 26 which is slidably fitted within the distal end 23 of the catheter 24. Sufficient proximal force on the drive wire 22 will overcome the frictional fit between the connection block 26 and the proximal end of the housing 42, thus moving the connection block 26 proximally (to the right on the page of FIGS. 15 and 16) to retract the connection block 26 within the tubular connector 24, as shown in FIG. 16. The catheter 24 can be used to provide a counterforce on the housing 42 while proximally retracting the drive wire 22 and connection block 26. Accordingly, the drive wire 22, catheter 24 and connection block 26 may be fully disconnected from the medical device 40, thereby leaving the first and second jaws 44, 46 and the housing 42 in a state having the tissue T clipped between the jaws 44, 46 and retained in vivo. The connection block 26 is retained at the distal end 23 of the catheter 24 via the pins 30, which are positioned within the recessed area 27 to engage the proximal and distal ends of the connection block 26 and limit its longitudinal movement.

The elongated catheter 24 (or other elongate tubular member such as a sheath, tube, scope or the like), which slidably encases the drive wire 22, extends proximally therealong to a proximal end of the system 20, and has a length suitable for placing the device 40 at any desired location within the body, while the proximal ends of drive wire 22 and catheter 24 are positioned outside of the body for use by the medical professional. Control handles (not shown) for controlling relative translation of the drive wire 22 and catheter 24 are well known in the art, and may be employed at the proximal end of the system 20.

Figure 17:
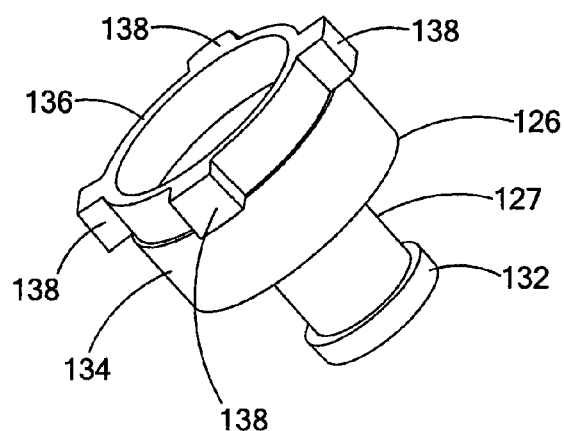
FIG. 17 is a perspective view of an alternate embodiment of a connection block forming a portion of the medical system of FIG. 1.
Figure 18:
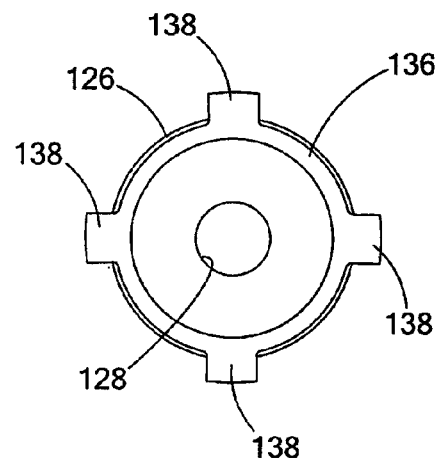
FIG. 18 is a front view showing the connection block of FIG. 17.

In another embodiment of a medical system 120 shown in FIGS. 17-22, a connection block 126 is slidably fitted within the distal end 23 of the catheter 24 (FIGS. 20-22) and defines a bore 128 therethrough (FIG. 18) which slidably receives the drive wire 22. As best seen in FIGS. 17-18, the exterior of the connection block 126 includes a recessed portion 127 defining a proximal flange 132 and a distal flange 134. In this embodiment, the distal flange 134 is larger than the proximal flange 132 (longitudinally), and it is slightly smaller than an inner diameter of the tubular housing 142 of the clip device 140 (i.e. does not have a friction fit). Here, a connection ring 136 is attached to the distal flange 134 and includes a plurality of tabs 138 which project radially outwardly and connect to the housing 142.

Figure 19:
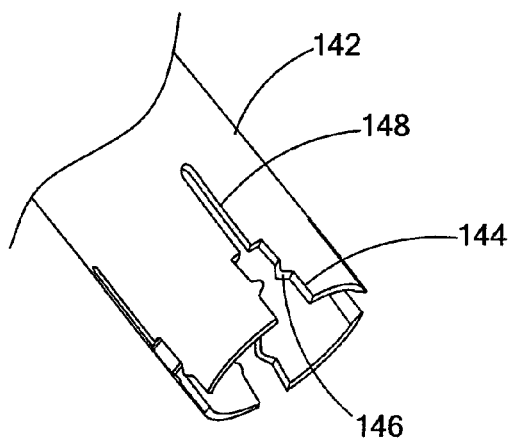
FIG. 19 is a perspective view of an alternate embodiment of the housing forming a portion of the medical system and medical device of FIG. 1.
Figure 20:
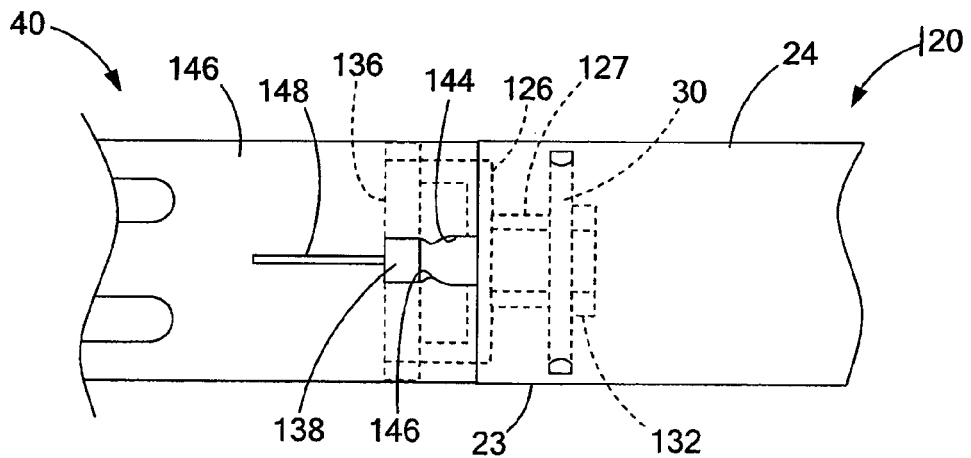
FIGS. 20-22 show steps of operating the medical system depicted in FIGS. 17-19.
Figure 21:
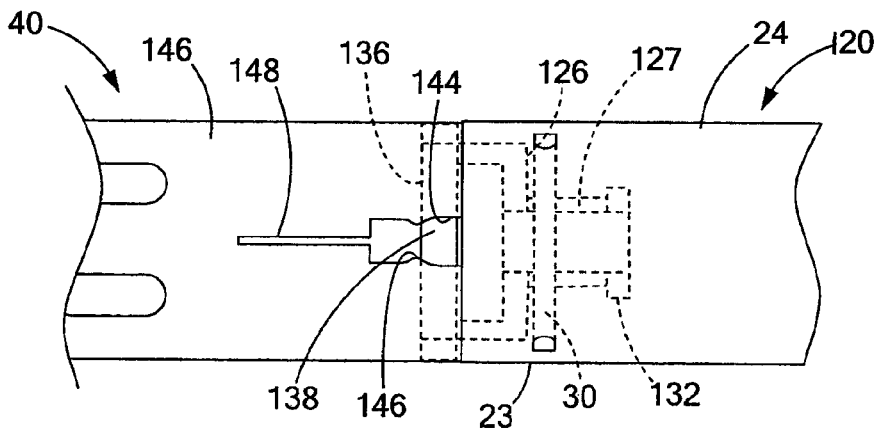
Figure 22:
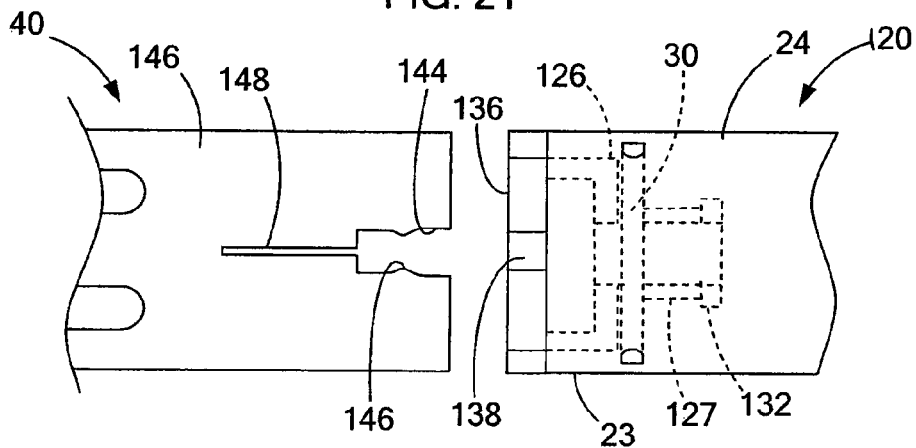

As best seen in FIG. 19, the proximal end of the housing 142 includes a plurality of slots 144 corresponding to the tabs 138 of the connection ring 136. The slots 144 extend longitudinally from the end surface of the housing 142 and include a narrowed region or throat 146 that is sized to retain the tabs 138 in a distal portion of the slots 144. A plurality of slits 148 may be formed in the housing 142 at the ends of the slots 144 to provide additional flexibility to allow the slots 144 to slightly enlarge as the tabs 138 pass through the throats 146 of the slots 144. The housing 142 may be formed of a suitable plastic or metal (or combination thereof) that is sufficiently flexible for passing the tabs 138 into the slots 144, while also being sufficiently rigid to form the guide surfaces which guide the jaws and driver as previously described. As shown in the sequence of FIGS. 20-22, the connection block is initially positioned within the proximal end of housing 142 such that the tabs 138 are locked into the distal portions of the slots 144 and held in place by the throat 146. When the drive wire 22 and its distal head 32 are retracted proximally to engage the connection block 126 (see, e.g., FIGS. 15-16), the connection block 126 is moved proximally relative to the housing 142 such that the tabs 138 move past the throats 146 and into the proximal portions of the slots 144, as shown in FIG. 21. With further proximal movement of the drive wire 22 and/or catheter 24, the clip device 40 may be detached from the catheter 24 and drive wire 22, as shown in FIG. 22.

Figure 23:
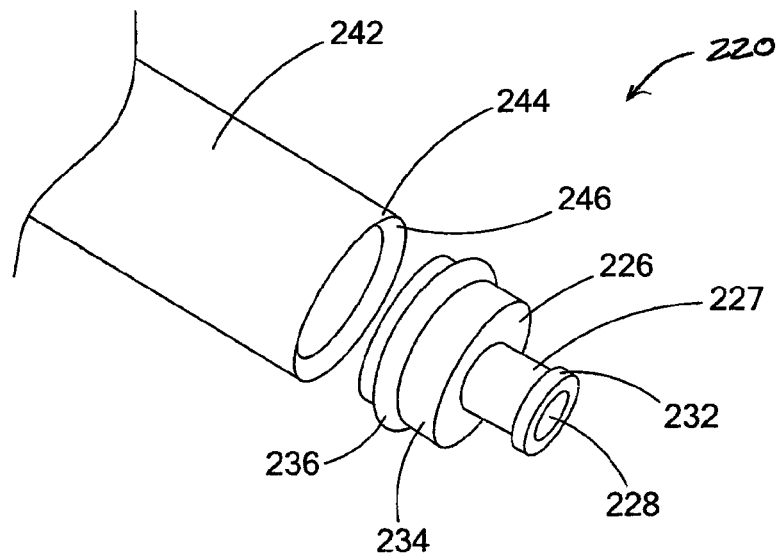
FIG. 23 is a perspective view of another alternate embodiment of a portion of the medical system and device depicted in FIG. 1.

In yet another embodiment of a connection block 226 for a medical system 220, shown in FIG. 23, the block 226 again includes a bore 228 and a recessed portion 227 defined by a proximal flange 232 and a distal flange 234. In this embodiment, the distal flange 234 is provided with an O-ring 236 or other similar gasket or compressible member (e.g. a disk or individual tabs made of an elastomer or rubber) that is fitted on the exterior of the distal flange 234. The connection block 226 may include a groove to receive the O-ring 236, or it may be attached via friction fit, adhesives, bonding techniques such as plastic welding, or other mechanical connecting structures. The O-ring 236 is sized to provide a friction fit between the connection block and the proximal end 244 of the housing 242. The proximal end 244 may also be formed with a chamfer 246 or other sloped surface to guide interconnection of the connection block 226 and the housing 242.

It will be recognized by those skilled in the art that the drive wire 22 and its distal head 32 could again be connected to the driver 48 and its socket 50, thus permitting additional manipulation of the medical device to adjust the clipped tissue T. Likewise, additional medical devices may be attached to the drive wire 22 and tubular connector 24 of the medical system 20 for deployment of the additional medical devices, e.g. multiple devices 40 for clipping the tissue T may be used to close a perforation or achieve hemostasis. Generally, the support ring 34 (FIGS. 1-4) fixed on the drive wire 22 can be used to limit the distal movement of the drive wire 22, and can be distally advanced to a position abutting the connection block 26. As such, the drive wire 22 and support ring 34 can be used to push the connection block 26 distally out of the tubular connector 24 so that it can be attached to the housing (e.g. 42) of a new medical device (e.g. 40), or the previously placed medical device 40. Alternatively, the user may manually press (i.e. with fingers or a tool) the connection block 26 distally out of the tubular connector 24 for connection to another medical device.

Figure 24:
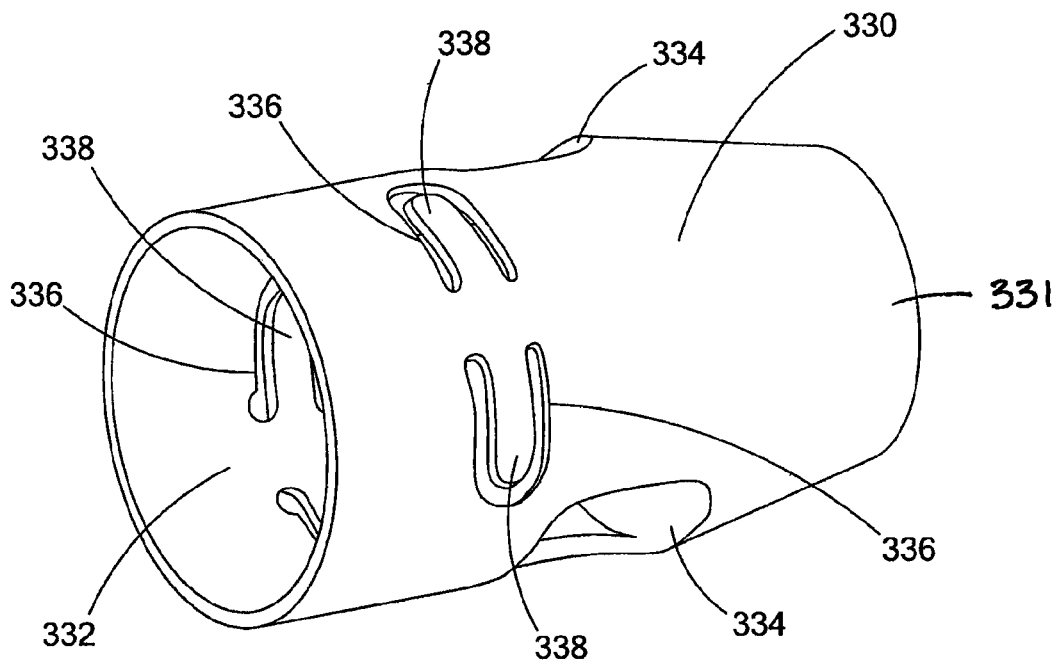
FIG. 24 is a perspective view of another embodiment of the medical system depicted in FIG. 1.
Figure 25:
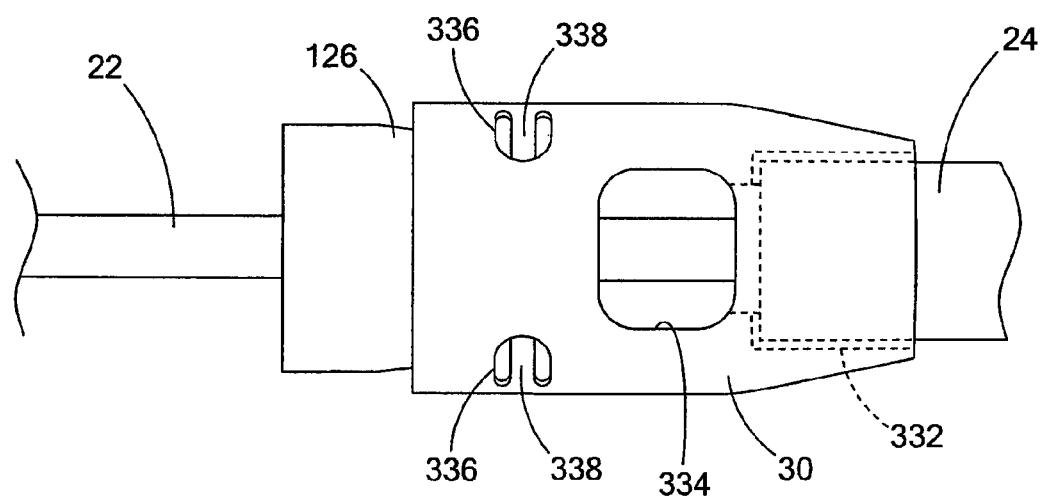
FIG. 25 is a side view of the medical system depicted in FIG. 24.

FIGS. 24-29 depict various alternate embodiments and devices that facilitate loading a clip device 40 within the medical system 20 in accordance with the foregoing. In FIG. 24, a catheter attachment 330 takes the form of a tubular member which defines an interior passageway 332 which extends therethrough. The proximal end 331 of the catheter attachment 330 is sized to be connected to the distal end of the catheter 24, as shown in FIG. 25 (e.g. via friction fit, adhesives, plastic bonding or welding, mechanical connectors, etc.). The catheter attachment 330 includes a pair of diametrically opposed openings 334 which provide access to the control wire 22 running through the catheter 24 and passageway 332, as best seen in FIG. 25. The catheter attachment 330 also includes U-shaped cut-outs 336 in four places, the cut-outs 336 leaving tabs 338. The tabs 338 may be bent radially inwardly as shown in FIG. 25, and thus can be used to replace the pin 30 in the catheter 24 shown in prior embodiments. That is, the tabs 338 project into the passageway 332 and fit within the recessed portion 127 of the connection plug 126 as was described with reference to FIG. 17-22. Like the pin 30, the tabs 338 limit the longitudinal movement of the connection block 126, while permitting rotation of the connected block 126 and the control wire 22 and catheter 24.

Figure 26:
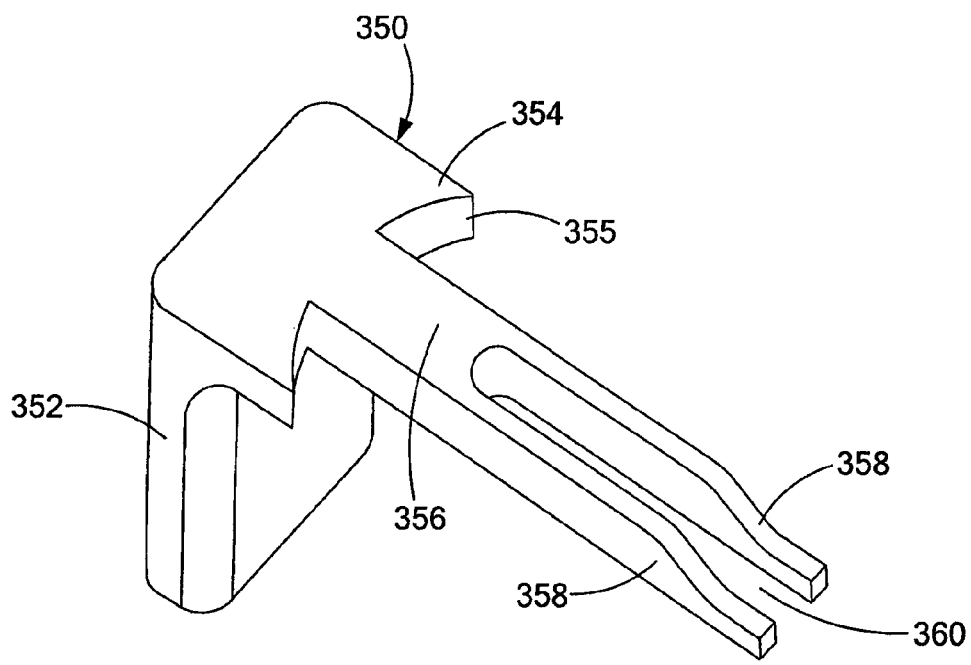
FIG. 26 is a perspective view of a locking pin forming a portion of the medical system depicted in FIGS. 21-25.

The large openings 334 in the catheter attachment 330 provide access to hold the connection block 126 in an extended position for attachment of another clip device 40. Turning to FIG. 26, a locking pin 350 is shown which may be positioned through the openings 334 and the catheter attachment 330 for holding the connection block 126 in its extended position shown in FIG. 25. The locking pin 350 includes a main body 352 having a flange 354 projecting laterally therefrom. From the flange 354 projects a forked strut 356 which also projects laterally from the main body 352. The forked strut 356 includes two tines 358 that are spaced apart to define a slot 360 therebetween. The slot 360 is sized to receive the drive wire 22 therein, and are also spaced to be entirely placed through the openings 334 in the catheter attachment 330. In this manner, the locking pin 350 prevents proximal movement of the connection block 126 to hold it in place for attachment of another device 40 for clipping the tissue.

Figure 27:
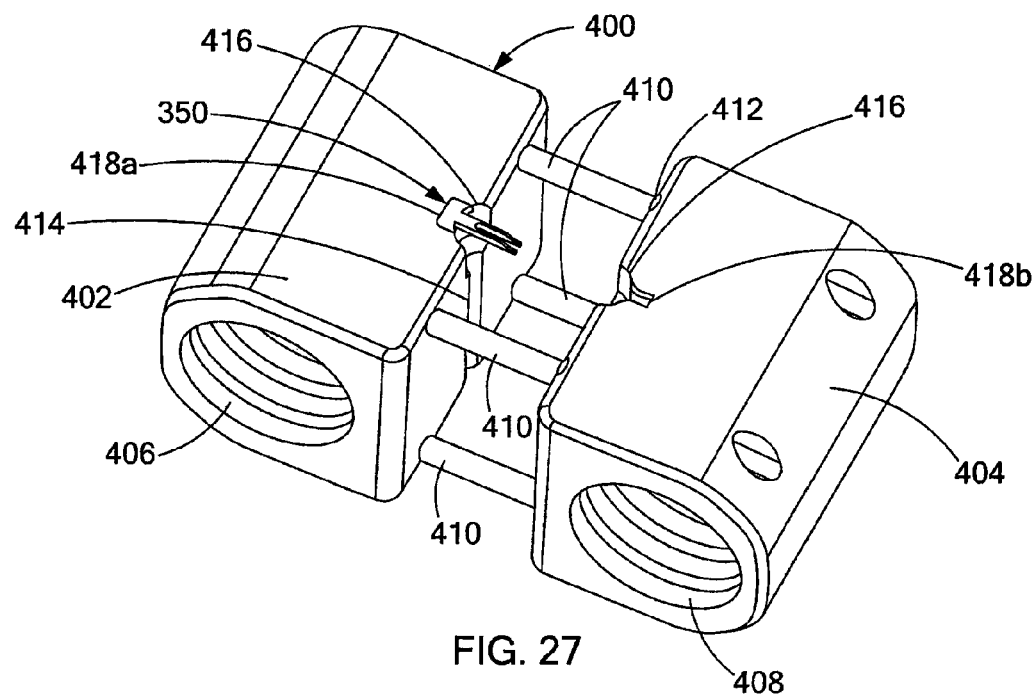
FIGS. 27-28 are perspective views showing operation of an applicator for the locking pin depicted in FIG. 26.
Figure 28:
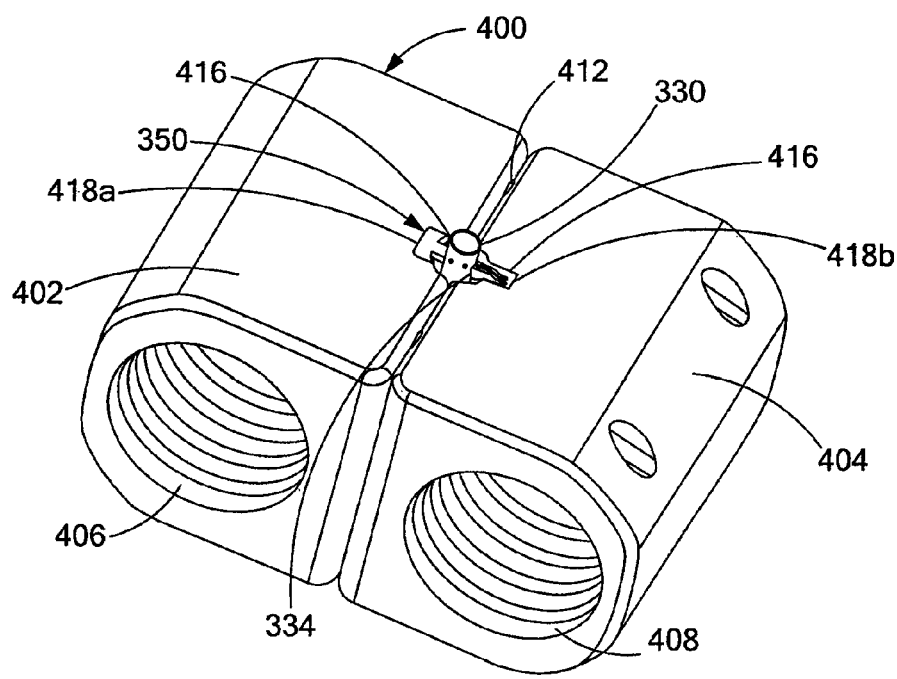

FIGS. 27 and 28 depict an applicator 400 for placing the locking pin 350 through the opening 334 in the catheter attachment 330. The applicator 400 generally includes a left body 402 and a right body 404, each of which define openings 406, 408 for receiving fingers of a medical professional. The left and right bodies 402, 404 are slidably connected to one another, for example using a plurality of rods 410 projecting from the left body 402 which are slidably received within passageways 412 formed in the right body 404. The left and right bodies 402, 404 also included channels for receiving the catheter 24 and catheter attachment 330 for placement of the locking pin 350. In particular, the channels include a lower portion 414 which is sized to receive the catheter 24, and an upper portion 416 which is sized to receive the catheter attachment 330. The upper channel portions 416 also include depressions which receive the locking pin 350, and in particular the left body 402 includes a recess 418a for receiving the main body 352 and flange 354 of the locking pin 350, while the right body 404 includes a recess 418b for receiving the ends of the tines 358 of the locking pin 350. Accordingly, and as shown in FIG. 28, the distal end of the catheter 24 and its catheter attachment 330 may be loaded in the channels 414, 416, of the right body 404, and then the left body 402 moved into engagement with the right body 404 such that the locking pin 350 is placed through the openings 334 in the catheter attachment 330 such that the tines 358 extend around the control wire 22 and the proximal movement of the connection block 126 is prevented, thus allowing the housing 42, 142 of a clip device 40, 140 to be pressed onto the connection block 26, 126, 226.

Figure 29:
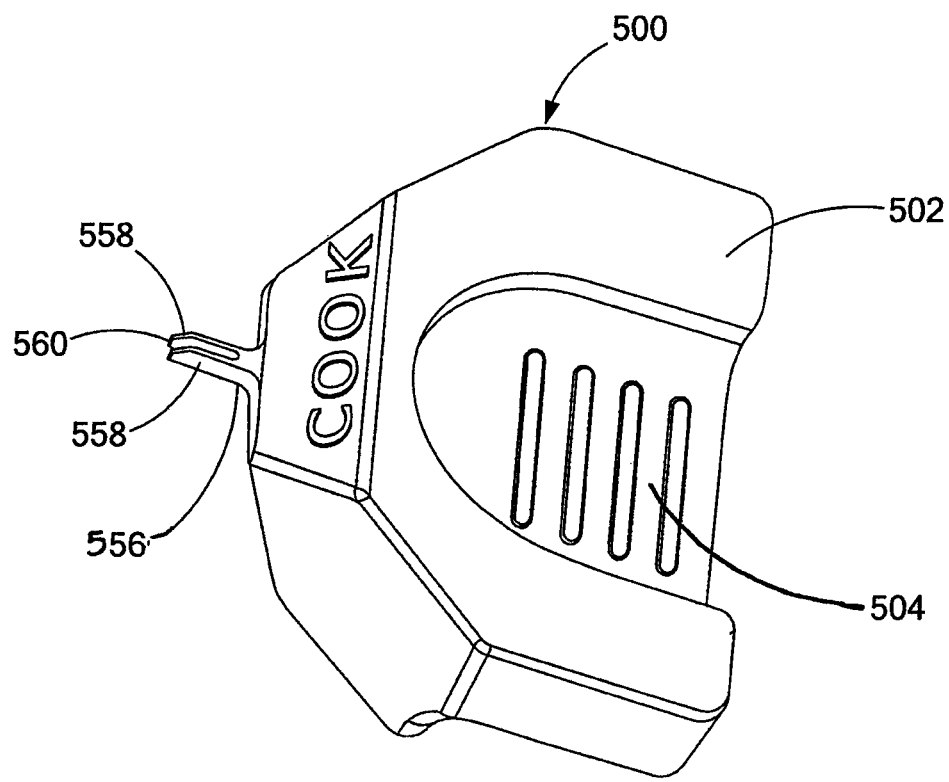
FIG. 29 is a perspective view of an alternate embodiment of the applicator depicted in FIGS. 27 and 28.

Finally, FIG. 29 depicts a perspective view of another embodiment of an applicator 500 for maintaining the connection block 26, 126, 226 in an extended position. As with the embodiment of FIGS. 24-28, the catheter 24 includes a catheter attachment 330 as previously described. Here, the applicator 500 is a single grasping member 502 which has recesses 504 on opposing sides for grasping between two fingers of the medical professional. The recesses 504 open to one side of the body 502, while the opposing side includes a fork strut 556 having two tines 558 spaced apart to define a slot 560. As with the prior embodiment, the tines 558 are sized to be passed through the openings 334 in the catheter attachment 330 such that the drive wire 22 is received within the slot 560, whereby proximal movement of the connection block 126 is blocked to maintain its extended position for attachment of another device 40 for clipping tissue.

Additional embodiments of the connection/disconnection mechanisms and the medical system 20 may be found in copending U.S. Appl. No. 61/391,875 and Appl. No. 61/391,881, the disclosures of which are hereby incorporated by reference in their entirety.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical system for engaging tissue, the medical system comprising:

a housing defining an internal passageway and a longitudinal axis extending between proximal and distal ends of the housing;

a first jaw rotatable relative to the housing, the first jaw having proximal and distal ends;

a second jaw rotatable relative to the housing, the second jaw having proximal and distal ends;

a driver engaged with the proximal ends of the first and second jaws, longitudinal movement of the driver rotating the first and second jaws relative to the housing;

an elongated drive wire selectively connected to the driver for longitudinal movement therewith, the drive wire having an enlarged portion proximate a distal end of the drive wire;

a tubular member defining a lumen sized to slidably receive a connection block, the connection block defining a bore slidably receiving the drive wire, the enlarged portion of the drive wire having a size that is larger than the bore and positioned on a distal side of the connection block; and the connection block operable between an extended position and a retracted position, the connection block projecting from the tubular member in the extended position and structured to engage a proximal end of the housing, the connection block positioned within the lumen of the tubular member in the retracted position and disengaged from the housing, wherein the enlarged portion of the drive wire engages the connection block upon proximal retraction of the drive wire to operate the connection block from its extended position to its retracted position and disengage the connection block from the housing.

2. The medical system of claim 1, wherein the connection block is sized to frictionally engage the housing.

3. The medical system of claim 1, wherein the connection block includes a connection ring having a plurality of tabs, and wherein the housing includes a plurality of slots extending to the proximal end of the housing that receive the plurality of tabs.

4. The medical system of claim 3, wherein the plurality of slots each include a narrowed throat separating proximal and distal portions of the slots.

5. The medical system of claim 3, wherein the housing further includes a plurality of slits formed therein, the slits each connected to a distal portion of the slots to improve flexibility of the housing.

6. The medical system of claim 1, wherein the connection block includes a distal flange and a proximal flange defining a reduced diameter portion therebetween, and wherein the tubular member includes one of a pin and a tab projecting into the lumen and positioned within the reduced diameter portion to limit longitudinal movement of the connection block.

7. The medical system of claim 1, wherein the connection block includes a compressible member attached thereto and sized to be compressed between an interior of the housing and an exterior of the connection block.

8. The medical system of claim 1, further comprising an attachment member attached to a distal end of the tubular member, the attachment member including a passageway in communication with the lumen of the tubular member.

9. The medical system of claim 8, wherein the attachment member includes diametrically opposing openings between ends of the attachment member in communication with the passageway.

10. The medical system of claim 9, further comprising a locking pin having a forked strut defined by two tines having a slot therebetween, the slot sized to receive the drive wire therein, the forked strut sized to pass through the opposing opening in the attachment member and limit longitudinal movement of the connection block.

11. The medical system of claim 10, further comprising an applicator having a left body slidably attached to a right body, the left and right bodies including channels sized and shaped to receive portions of the tubular member and attachment member and maintain their position relative to the applicator, the channels further sized and shaped to receive portions of the locking pin, whereby relative translation of the left and right bodies positions the forked strut of the locking pin into, or out of, the opposing openings in the attachment member.

12. The medical system of claim 11, wherein the left and right bodies each include openings sized to receive fingers of a medical professional.

13. The medical system of claim 9, further comprising an applicator having a main body and a forked strut projecting from the main body, the forked strut defined by two tines having a slot therebetween, the slot sized to receive the drive wire therein, the forked strut sized to pass through the opposing opening in the attachment member and limit longitudinal movement of the connection block.

14. The medical system of claim 13, wherein the main body includes recesses on opposing sides of the main body, the recesses sized to receive fingers of a medical professional.

15. The medical system of claim 8, wherein the connection block includes a distal flange and a proximal flange defining a reduced diameter portion therebetween, and wherein the attachment member includes at least one tab projecting into the lumen and positioned within the reduced diameter portion to limit longitudinal movement of the connection block, the tab unitarily and integrally formed with the attachment member.

16. The medical system of claim 1, wherein the enlarged portion of the drive wire is an enlarged distal head, and wherein the driver includes a socket facing proximally, the driver constructed of a resilient material that flexes to adjust the size of the socket, the socket sized to selectively receive the enlarged distal head of the drive wire.

17. The medical system of claim 16, wherein the driver includes a locking tab positioned at an entrance to the socket that moves to vary the size of the entrance.

18. The medical system of claim 17, wherein the driver includes two locking tabs on opposing sides of the socket, and wherein the housing includes a guide surface guiding the longitudinal movement of the driver, the guide surface including two surfaces on opposing sides of the housing corresponding to the two locking tabs.

19. The medical system of claim 18, wherein the housing defines a shoulder at a transition between a proximal portion and a distal portion of the guide surface, and wherein the locking tabs are positioned to engage the shoulder to limit longitudinal movement of the driver.

20. The medical system of claim 19, wherein the shoulder deflects the tab to a position into engagement with the shoulder when a distally directed longitudinal force on the driver reaches a predetermined force to permit longitudinal movement of the driver and the first and second jaws in a distal direction.

* * * * *